(12) United States Patent
Delambre et al.

(10) Patent No.: US 6,784,145 B2
(45) Date of Patent: Aug. 31, 2004

(54) COSMETIC AND DERMATOLOGICAL ARTICLE COMPRISING N-(3-CHLOROALLYL) HEXAMINIUM CHLORIDE

(75) Inventors: Patricia Delambre, Ablon-sur-Seine (FR); Philippe Touzan, Paris (FR); Pascal Simon, Vitry sur Seine (FR)

(73) Assignee: L'Oreal, Paris (FR)

( * ) Notice: Subject to any disclaimer, the term of this patent is extended or adjusted under 35 U.S.C. 154(b) by 91 days.

(21) Appl. No.: 10/175,378

(22) Filed: Jun. 20, 2002

(65) Prior Publication Data

US 2003/0027738 A1 Feb. 6, 2003

(30) Foreign Application Priority Data

Jun. 22, 2001 (FR) .............................. 01 08284

(51) Int. Cl.[7] .............................................. C11D 17/00
(52) U.S. Cl. ..................... 510/130; 510/136; 510/295; 510/296; 510/438; 510/480; 510/499; 510/504
(58) Field of Search ................................ 510/130, 136, 510/480, 295, 296, 438, 499, 504, 426; 424/401, 402

(56) References Cited

U.S. PATENT DOCUMENTS

| 5,141,803 A | 8/1992 | Pregozen |
|---|---|---|
| 5,747,052 A | 5/1998 | Mimikos et al. |
| 6,063,388 A * | 5/2000 | Bui-Bertrand et al. ...... 424/401 |
| 6,432,429 B1 * | 8/2002 | Maddern et al. ............ 424/402 |

FOREIGN PATENT DOCUMENTS

| EP | 0 850 634 A1 | 7/1998 |
|---|---|---|
| NL | 7 102 420 | 8/1972 |
| WO | WO 01/53443 A1 | 7/2001 |

OTHER PUBLICATIONS

P. Alexander; "Preservatives in Personal Care Products"; Soap Perfumery and Cosmetics, United Trade Press Ltd., London, GB; vol. 60, No. 3; Mar. 1, 1987; pp. 47–49.
International Cosmetic Ingredient Dictionary and Handbook, Eighth Edition 2000; vol. 2; p. 1259.

* cited by examiner

*Primary Examiner*—Nechoulus Ogden
(74) *Attorney, Agent, or Firm*—Oblon, Spivak, McClelland, Maier & Neustadt, P.C.

(57) ABSTRACT

The invention relates to an article containing (A) a water-insoluble substrate and (B) containing an aqueous phase and N-(3-chloroallyl)hexaminium chloride. According to one preferred embodiment of the invention, the composition also contains at least one $C_1$–$C_4$ alkyl para hydroxybenzoate and/or at least one ethylenediamine-tetraacetic acid salt. The article may especially constitute a wipe for cleansing and/or removing makeup from the facial and/or body skin, and also for removing makeup from the eyes. The wipe may be in the form of a moist or dry wipe.

30 Claims, No Drawings

COSMETIC AND DERMATOLOGICAL ARTICLE COMPRISING N-(3-CHLOROALLYL) HEXAMINIUM CHLORIDE

BACKGROUND OF THE INVENTION

1. Field of the Invention

The invention relates to an article, preferably a wipe, comprising (A) a water-insoluble substrate, and (B) a composition added to, impregnated onto, in contact with, etc. the substrate comprising an aqueous phase and N-(3-chloroallyl)hexaminium chloride (Quatemium-15). The invention also includes the uses of this article in cosmetics or dermatology, in particular for cleansing and/or removing makeup from the skin, more especially of the face, and of the eyes.

2. Background of the Invention

For cleansing or removing makeup from the skin, it is known practice to use compositions of the lotion or milk type which are applied to a cotton-wool support at the time of use, and applied to the face.

It is also known practice to use moist wipes which contain an impregnation composition for cleansing or removing makeup from the skin, thus avoiding the handling and transportation of bottles containing lotions or milks. These wipes generally consist of a substrate made of a material of natural or synthetic origin, which is preferably nonwoven, impregnated with a composition that is suited to the desired aim, for example cleansing or removing makeup from the skin.

The compositions for impregnating these wipes generally contain water and can be, for example, in the form of solutions, dispersions or emulsions. Due to the presence of water in these compositions, it is necessary to protect them against the growth and proliferation of microorganisms by introducing preserving agents therein. Specifically, such a growth of microorganisms would rapidly make the compositions, and consequently the articles containing them, unsuitable for use.

The chemical preserving agents most commonly used in this field are especially $C_1$–$C_4$ alkyl para-hydroxybenzoates, referred to hereinbelow as parabens, and phenoxyethanol. Unfortunately, these preserving agents have the drawback of needing to be used at high doses to provide an effective antibacterial protection on supports such as wipes, and often at doses that are higher than in the case of makeup-removing milks and lotions presented in bottles. These preserving agents in larger amounts can give rise to intolerance on human skin, such as irritations and/or allergies, and more especially on sensitive skin.

OBJECT OF THE INVENTION

There is a need for a preserving system whose antibacterial efficacy on substrate-containing articles such as wipes is at least as effective as the systems of the prior art in the same concentration ranges, but not having their drawbacks and especially not being irritant to the skin or the eyes.

SUMMARY OF THE INVENTION

The Inventors have found, surprisingly, that the use of N-(3-chloroallyl)hexaminium chloride, also called 1-(3-chloroallyl)-3,5,7-triazo-1-azoniamadamantane chloride (also known by the CTFA name: Quaternium-15), even in a very little amount, gives particularly effective protection against microorganisms (e.g., bacteria, yeasts and moulds) and produces a composition that is suitable for impregnation onto a support.

Certainly, Quaternium-15 is known as preservative in cosmetic compositions. Thus, the document EP-850634 describes a preservative system comprising Quaternium-15. However, the bacteriological protection of a wipe poses specific problems by the fact that the contact surface with air is much greater than the contact surface of a product which is in a jar or in a flask, that increases the risk of contamination and, thus, needs a better bacteriological protection. Thus, one problem solved by the invention was to get a good efficacy of bacteriological protection while having a low amount of preservative in order to have a lower irritation.

DETAILED DESCRIPTION OF THE INVENTION

Thus, one subject of the present invention is a wipe for the skin comprising (A) a nonwoven water-insoluble substrate and (B) a composition in contact with, added to, or impregnated onto the substrate, comprising preferably in a physiologically acceptable medium, an aqueous phase and from 0.01% to 0.05% by weight of N-(3-chloroallyl)hexaminium chloride (i.e., Quaternium 15) relative to the total weight of the composition, preferably 0.01 to 0.03% by weight.

This article (wipe) is preferably suitable for skincare and/or skin treatment and is especially a cleansing wipe or makeup-removing wipe for body skin, and/or a cleansing wipe or makeup-removing wipe for the eyes, and also for cleansing greasy skin or acne-prone skin.

A subject of the invention is thus also the cosmetic and dermatologic use of the wipe as defined above for cleansing and/or removing makeup from the skin and/or the eyes, for cleansing generally, applying an active agent, etc.

Another subject of the invention is the cosmetic use of 0.01% to 0.05% by weight of N-(3-chloroallyl)hexaminium chloride relative to the total weight of the composition, as an agent for combating microorganisms in a cosmetic composition containing an aqueous phase and intended to contact, impregnate, etc. a nonwoven water-insoluble substrate.

The article (wipe) obtained may be used for example to treat greasy skin and/or to disinfect the skin and to purify it in the event of the presence of acne spots, especially if it contains antimicrobial agents.

A subject of the invention is also the use of a wipe as defined above, for cleansing greasy skin or acne-prone skin.

The composition used according to the invention generally comprises from 0.01% to 0.05% and preferably from 0.01% to 0.03% by weight of Quaternium-15 relative to the total weight of the composition.

According to one preferred embodiment of the invention, the composition used on the substrate may also comprise at least one other preserving agent, for example one chosen from $C_1$–$C_4$ alkyl para-hydroxybenzoates and ethylenediaminetetraacetic acid salts, and mixtures thereof.

The $C_1$–$C_4$ alkyl para-hydroxybenzoates include in particular methyl para-hydroxybenzoate, referred to hereinbelow as methylparaben, ethyl parahydroxybenzoate, referred to hereinbelow as ethylparaben, and propyl para-hydroxybenzoate, referred to hereinbelow as propylparaben, and mixtures thereof. According to one preferred embodiment of the invention, it is methylparaben or propylparaben. Methylparaben is more particularly preferred.

The invention article may comprise, for example, from 0.01% to 0.3% by weight and preferably from 0.05% to 0.25% by weight of alkyl para hydroxybenzoate relative to the total weight of the composition.

The ethylenediaminetetraacetic acid salts include alkali metal salts and most especially the sodium salt. According to one preferred embodiment of the invention, it is the disodium salt of ethylenediaminetetraacetic acid or the tetrasodium salt of ethylenediaminetetraacetic acid, or mixtures thereof.

The composition according to the invention may comprise, for example, from 0.01% to 0.2% by weight and preferably from 0.05% to 0.15% by weight of ethylenediaminetetraacetic acid salt relative to the total weight of the composition.

The preserving system comprising N-(3-chloroallyl) hexaminium chloride and also the $C_1$–$C_4$ alkyl para-hydroxybenzoate and/or the ethylenediaminetetraacetic acid salt, generally represents in total from 0.025% to 0.55% by weight and better still from 0.1% to 0.3% by weight relative to the total weight of the composition.

The composition used according to the invention for the impregnation of the water-insoluble substrate preferably is a physiologically acceptable medium, that is to say a medium that is compatible with the skin, mucous membranes, the hair and the scalp. The aqueous medium of the composition used according to the invention may contain, besides water, one or more solvents chosen from lower alcohols containing from 1 to 6 carbon atoms, such as ethanol; polyols such as glycerol; glycols, for instance butylene glycol, isoprene glycol, hexylene glycol, propylene glycol or polyethylene glycols such as PEG-8; sorbitol; sugars such as glucose, fructose, maltose, lactose or sucrose; and mixtures thereof.

According to one preferred embodiment of the invention, the composition intended to contact, impregnate, etc. a support has a viscosity that is preferably less than 150 mPa.s and more preferably less than 100 mPa.s. This viscosity preferably ranges from 1 mPa.s to 100 mPa.s, measured at room temperature (about 25° C.) with a Rheomat RM 180 machine, using a No 1 spindle. The composition used according to the invention preferably has a pH ranging from 3 to 7.5 and more preferably from 6 to 7.5 and better from 6 to 7.

The compositions according to the invention may be in any presentation form, most preferably a form that is suitable for topical application, especially in the form of aqueous or aqueous-alcoholic solutions, lotions, milks, aqueous or aqueous-alcoholic gels, emulsions obtained by dispersing a fatty phase in an aqueous phase (O/W) or, conversely, (W/O), suspensions, microemulsions, microcapsules, microparticles or vesicular dispersions of ionic type (liposomes) and/or nonionic type.

According to one preferred embodiment of the invention, the composition is in the form of an O/W emulsion and constitutes a lotion or a milk.

When the composition used according to the invention is an emulsion, the proportion of the fatty phase (or oily phase) is not limited and may range from 5% to 80% by weight and preferably from 5% to 50% by weight relative to the total weight of the composition. The oils, emulsifiers and co-emulsifiers used in the composition in emulsion form are not limited and may be chosen from those conventionally used in cosmetics or dermatology. The emulsifier and optionally the co-emulsifier are preferably present in the composition in a proportion ranging from 0.3% to 30% by weight and more preferably from 0.5% to 20% by weight relative to the total weight of the composition. The fatty phase or oily phase usually contains at least one oil. Oils that may be used in the composition of the invention include, for example:

- hydrocarbon-based oils of animal origin, such as perhydrosqualene;
- hydrocarbon-based oils of plant origin, such as liquid triglycerides of fatty acids containing from 4 to 10 carbon atoms, for instance heptanoic or octanoic acid triglycerides or alternatively, for example, sweet almond oil, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil or karite butter oil;
- synthetic esters and synthetic ethers, especially of fatty acids, for instance oils of formulae $R^1COOR^2$ and $R^1OR^2$ in which $R^1$ represents a fatty acid residue containing from 8 to 29 carbon atoms and $R^2$ represents branched or unbranched hydrocarbon-based chain containing from 3 to 30 carbon atoms, such as, for example, purcellin oil, isononyl isononanoate, isopropyl myristate, isopropyl palmitate, 2-ethylhexyl palmitate (or octyl palmitate), 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;
- linear or branched hydrocarbons of mineral or synthetic origin, such as volatile or non-volatile liquid paraffins, and derivatives thereof, petroleum jelly, polydecenes, and hydrogenated polyisobutene such as Parleam® oil;
- fatty alcohols containing from 8 to 26 carbon atoms, for instance cetyl alcohol, stearyl alcohol and a mixture thereof (cetearyl alcohol), octyldodecanol, 2-butyloctanol, 2-hexyldecanol, 2-undecylpentadecanol, oleyl alcohol or linoleyl alcohol;
- alkoylated and especially ethoxylated fatty alcohols such as oleth-12 or ceteareth-20;
- partially hydrocarbon-based and/or silicone-based fluoro oils, for instance those described in document JP-A-2 295 912. Examples of fluoro oils which may also be mentioned include perfluoromethylcyclopentane and perfluoro-1,3-dimethylcyclohexane, sold under the names "Flutec PC1®" and "Flutec PC3®" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the company 3M, or alternatively bromoperfluorooctyl sold under the name "Foralkyl®" by the company Atochem; nonafluoromethoxybutane sold under the name "MSX 4518®" by the company 3M and nonafluoroethoxyisobutane; perfluoromorpholine derivatives, such as the 4-trifluoromethylperfluoromorpholine sold under the name "PF 5052®" by the company 3M;
- silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane; polydimethylsiloxanes comprising alkyl, alkoxy or phenyl groups, that are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyl-trimethylsiloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

The composition according to the invention may contain ionic or nonionic emulsifiers, the choice of which depends on the desired emulsion (W/O or O/W). Emulsifiers that may be used are those usually used in the field under consideration.

Useful emulsifiers include nonionic surfactants such as fatty acid esters of polyols, and oxyalkylenated and especially oxyethylenated derivatives thereof; fatty acid ethers of polyols, and oxyalkylenated and especially oxyethylenated derivatives thereof, and mixtures thereof. When they are oxyalkylenated fatty acid esters of polyols or oxyalkylenated fatty alcohol ethers of polyols, there may be, for example, from 1 to 150 oxyalkylenated and especially oxyethylenated groups. Emulsifiers that may be mentioned more particularly include the mixture of glyceryl stearate and of PEG-100 stearate sold under the name Arlacel 165 by the company ICI; polyoxyethylenated fatty alcohol ethers comprising from 1 to 100 oxyethylenated groups, such as, for example, ceteareth-12 and ceteareth-20, and also mixtures containing them, for instance the mixture sold under the name Emulgade CM by the company Henkel (mixture of cetearyl isononanoate, ceteareth-20, cetearyl alcohol, glyceryl stearate, glycerol, ceteareth-12 and cetyl palmitate. The emulsifiers mentioned above are used for the preparation of O/W emulsions.

Nonionic, anionic, amphoteric or zwitterionic surfactants, that promote the removal of makeup and impurities and that make the composition foaming, may also be added to the composition of the invention. They may especially be foaming surfactants. Surfactants of this type that may be mentioned, for example, include: (1) among nonionic surfactants, oxyethylenated oxypropylenated block polymers such as Poloxamer 184 (CTFA name); alkylpolyglycosides and especially alkylpolyglucosides (APG) with an alkyl group containing from 6 to 30 carbon atoms ($C_6$–$C_{30}$-alkyl polyglucosides) and preferably 8 to 16 carbon atoms, such as, for example, decylglucoside (C9/C11-alkylpolyglucoside (1.4) such as the product sold under the name Mydol 10 by the company Kao Chemicals, the product sold under the name Plantaren 2000 UP or Plantacare 2000 UP by the company Henkel, and the product sold under the name Oramix NS 10 by the company SEPPIC; caprylyl/capryl glucoside, for instance the product sold under the name Oramix CG 110 by the company SEPPIC; laurylglucoside, for instance the products sold under the names Plantaren 1200 N and Plantacare 1200 by the company Henkel; and cocoglucoside, for instance the product sold under the name Plantacare 818/UP by the company Henkel;

(2) among anionic surfactants, alkyl sulphates, alkyl ether sulphates and salts thereof, especially the sodium salts thereof, for instance the mixture of sodium laureth sulphate/magnesium laureth sulphate/sodium laureth-8 sulphate/magnesium laureth-8 sulphate, sold under the name Texapon ASV by the company Henkel; sodium lauryl ether sulphate (70/30 C12–14) (2.2 EO) sold under the names Sipon AOS 225 or Texapon N702 Paste by the company Henkel, ammonium lauryl ether sulphate (70/30 C12–C14) (3 EO) sold under the name Sipon LEA 370 by the company Henkel; ammonium (C12–C14)alkyl ether (9 EO) sulphate sold under the name Rhodapex AB/20 by the company Rhodia Chimie;

(3) among amphoteric or zwitterionic surfactants, alkylamido alkylamine derivatives such as N-disodium N-cocoyl-N-carboxymethoxyethyl-N-carboxymethylethylenediamine (CTFA name: disodium cocoamphodiacetate) sold as an aqueous saline solution under the name Miranol C2M CONC NP by the company Rhodia Chimie; N-sodium N-cocoyl-N-hydroxyethyl-N-carboxy-methylethylenediamine (CTFA name: sodium cocamphoacetate) and the mixture of coconut acid ethanolamides (CTFA name: Cocoamide DEA).

The composition may also comprise a mixture of these surfactants.

The composition used to contact, impregnate, etc. the substrate may also comprise adjuvants conventionally used in the fields under consideration, such as, for example, organic solvents, solubilizing agents, hydrophilic or lipophilic thickeners and gelling agents, softeners, antioxidants, opacifiers, stabilizers, foaming agents, fillers, chelating agents, fragrances, screening agents, essential oils, dyestuffs, pigments, hydrophilic or lipophilic active agents, lipid vesicles optionally encapsulating one or more active agents, or any other ingredient usually used in cosmetics or dermatology. It may optionally also contain preserving agents other than those mentioned above. The amounts of the various constituents of the compositions according to the invention are those conventionally used in the fields under consideration. Needless to say, these adjuvants must be of a nature and used in an amount such that they not disrupt the preserving system according to the invention. The amount of these adjuvants may range, for example, from 0.01% to 30% by weight relative to the total weight of the composition.

Active agents may be present in the invention composition including, for example, without this list being limiting, antiseborrhoeic active agents for cleaning the excess sebum on the skin, and antimicrobial agents that remove from the skin any microorganisms that may be present thereon, and mixtures thereof.

Antiseborrhoeic active agents that may be mentioned include, for example, sulphur and sulphur derivatives, benzoyl peroxide, zinc derivatives such as zinc sulphate and zinc oxide, aluminium chloride, selenium disulphide, B vitamins and especially panthenol (vitamin B5) and niacinamide (vitamin B6 or PP), and mixtures thereof.

Useful active agents include, for example, antimicrobial agents: β-lactam derivatives, quinolone derivatives, ciprofloxacin, norfloxacin, tetracycline and its salts (hydrochloride), erythromycin and its salts (zinc, estolate or stearate salt), amikacin and its salts (sulphate), 2,4,4'-trichloro-2'-hydroxydiphenyl ether (triclosan), 3,4,4'-trichlorobanilide (tricarban), phenoxyethanol, phenoxypropanol, phenoxyisopropanol, doxycycline and its salts (hydrochloride), capreomycin and its salts (sulphate), chlorhexidine and its salts (gluconate, hydrochloride), chlorotetracycline and its salts (hydrochloride), oxytetracycline and its salts (hydrochloride), clindamycin and its salts (hydrochloride), ethambutol and its salts (hydrochloride), hexamidine and its salts (isethionate), metronidazole and its salts (hydrochloride), pentamidine and its salts (hydrochloride), gentamycin and its salts (sulphate), kanamycin and its salts (sulphate), lineomycin and its salts (hydrochloride), methacycline and its salts (hydrochloride), methenamine and its salts (hippurate, mandelate), minocycline and its salts (hydrochloride), neomycin and its salts (sulphate), netilmicin and its salts (sulphate), paromomycin and its salts (sulphate), streptomycin and its salts (sulphate), tobramycin and its salts (sulphate), miconazole and its salts (hydrochloride), amanfadine and its salts (sulphate, hydrochloride), octopirox, para-chloro-meta-xylenol, nystatin, tolnaftate, zinc pyrithione, clotrimazole, salicylic acid, 5-n-octanoylsalicylic acid (or capryloylsalicylic acid), benzoyl peroxide, 3-hydroxybenzoic acid, glycolic acid, lactic acid, 4-hydroxybenzoic acid, acetylsalicylic acid, 2-hydroxybutanoic acid, 2-hydroxypentanoic acid, 2-hydroxyhexanoic acid, phytic acid, N-acetyl-L-cysteine acid, lipoic acid, azelaic acid, arachidonic acid, ibuprofen, naproxen, hydrocortisone, acetaminophen, resorcinol, lidocaine hydrochloride, neomycin sulphate, octoxyglycerol, octanoylglycine (or capryloylglycine), caprylylglycol (1,2-octanediol) and 10-hydroxy-2-decanoic acid, and mixtures thereof.

The preferred microbial agents are 2,4,4'-trichloro-2'-hydroydiphenyl ether, 3,4,4'-trichloro-banilide, phenoxyethanol, phenoxypropanol, phenoxyisopropanol, chlorhexidine and its salts, octopirox, zinc pyrithione, salicylic acid, 5-n-octanoylsalicylic acid, benzoyl peroxide, 3-hydroxybenzoic acid, glycolic acid, lactic acid, 4-hydroxybenzoic acid, acetylsalicylic acid, 2-hydroxybutanoic acid, 2-hydroxypentanoic acid, 2-hydroxyhexanoic acid, phytic acid, N-acetyl-L-cysteine acid, lipoic acid, azelaic acid, arachidonic acid, octoxyglycerol, octanoylglycine, caprylyl glycol, 10-hydroxy-2-decanoic acid, and mixtures thereof.

Hydrophilic gelling agents useful herein include in particular carboxyvinyl polymers such as carbomers; modified acrylic copolymers such as acrylate/alkylacrylate copolymers, for instance the products sold under the name Pemulen by the company Goodrich; polyacrylamides, for instance the product sold under the name Sepigel 305 by the company SEPPIC, or poly(2-acrylamido-2-methylpropanesulphonic acid) sold by the company Hoechst under the trade name "Hostacerin AMPS" (CFTA name: ammonium polyacryldimethyltauramide); polysaccharides, especially cellulose derivatives and natural gums, for instance xanthan gum or guar gum; and clays. Lipophilic gelling agents that may be mentioned include modified clays, for instance bentones, metal salts of fatty acids, hydrophobic silica, polyethylenes, and mixtures thereof. Gelling agents that may also be used include polymers with a hydrophobic function, such as polysaccharides with a hydrophobic chain, for instance quatemized guar gums.

The composition according to the present invention is advantageously free from 2-pyrrolidone-5 carboxylic acid.

The compositions according to the invention can be prepared according to techniques that are well known to those skilled in the art, in view of this disclosure.

According to one particular embodiment of the invention, the composition is in the form of a PIT emulsion. The principle of this technique for obtaining an O/W emulsion is well known to those skilled in the art and is especially described in the articles "Phase inversion emulsification" by Th. Förster et al. published in Cosmetics & Toiletries, Vol. 106, December 1991, pp. 49–52, "Application of the phase-inversion-temperature method to the emulsification of cosmetics" by T. Mitsui et al. published in American Cosmetics and Perfumery, vol. 87, December 1972. Its principle is as follows: a W/O emulsion is prepared (introduction of the water into the oil) at a temperature which must be greater than the phase inversion temperature (PIT) of the system, that is to say the temperature at which the equilibrium between the hydrophilic and lipophilic properties of the emulsifier(s) used is achieved; at elevated temperature (>PIT), the emulsion is of water-in-oil type, and, during its cooling, at the phase inversion temperature, this emulsion inverts to become an emulsion this time of oil-in-water type, and does so by passing beforehand through a microemulsion state. This technique gives "ultrafine" O/W emulsions, in which the mean size of the globules constituting the fatty phase is within well-defined limits, i.e. between 50 and 1 000 nm. These emulsions are extremely fluid and are particularly suitable for impregnating water-insoluble substrates so as to constitute cleansing articles or wipes.

According to one particular embodiment, the PIT emulsion is prepared in concentrated form and then diluted, generally just before impregnation, with a fresh portion of an aqueous phase that may also contain all or some of the predissolved preserving agents.

The water-insoluble substrate is preferably chosen from the group of nonwoven materials. It may especially be a nonwoven substrate based on fibres of natural origin (flax, wool, cotton or silk) or of synthetic origin (cellulose derivatives, viscose, polyvinyl derivatives, polyesters such as polyethylene terephthalate, polyolefins such as polyethylene or polypropylene, polyamides such as Nylon, or acrylic derivatives). The nonwovens are described in general in Riedel "Nonwoven bonding methods & materials", Nonwoven World (1987). These substrates are obtained according to the usual processes of the technique for preparing nonwovens. According to one particular embodiment of the invention, the insoluble substrate may contain at least one of the preserving agents of the invention, bound to the support by known means for grafting biocidal agents to fibres.

This substrate may comprise one or more layers that have identical or different properties, and may have elasticity, softness and other properties that are suitable for the desired use. The substrates may comprise, for example, two parts having properties of different elasticity, as described in document WO-A-99/13861 or may comprise a single layer with different densities, as described in document WO-A-99/25318, or may comprise two layers of different textures, as described in document WO-A-98/18441.

The substrate may have any size and any shape that is suitable for the desired aim. It generally has a surface area of between 0.005 m$^2$ and 0.1 m$^2$ and preferably between 0.01 m$^2$ and 0.05 m$^2$. It is preferably in the form of rectangular wipes or round compresses.

The final article comprising the substrate and the composition is generally in the moist state, with a degree of impregnation, contact, etc. of the composition ranging, for example, from 200% to 1000% and preferably from 250% to 350% by weight of composition relative to the weight of substrate. The techniques for contacting, impregnating, etc. the substrates with compositions are well known in this field and are all applicable to the present application. In general, the impregation composition is added to the substrate by one or more techniques comprising immersion, coating, vaporization, etc.

It is also possible to make a wipe in dry form either by removing the water from the composition after it has been impregnated onto the substrate, or by impregnating the substrate with a composition in dry form, in the form of a powder, granule or film, by any known production means, for instance welding and bonding multilayers thermally or by ultrasound, In this last embodiment, the composition is dried by any known means: spraying, freeze-drying or another similar process.

Moist wipes or dry wipes may thus be obtained according to the intended use. The moist wipes may be used in unmodified form, while the dry wipes can be moistened before use.

Another subject of the invention is a kit comprising the substrate and composition in physically separate forms, the substrate and composition being brought into contact before use.

A further subject of the invention is a cosmetic process for cleansing and/or removing makeup from the skin and/or the eyes, which consists in passing an article as defined above over the skin and/or the eyes.

Throughout the text hereinbelow, the percentages are given on a weight basis, except where otherwise mentioned.

Other characteristics and advantages of the invention may emerge in the examples that follow, which are given purely as illustrations and with no limiting nature.

Test

The following test demonstrates the activity of the combination according to the invention on microorganisms.

The steps for performing this test are as follows:

1st step: on the fluid alone

1) Microorganism culture of the strains used:

*Enterococcus faecalis* (bacterium)

*Candida albicans* (yeast)

*Aspergillus niger* (mould)

The strains are prepared in the tryptone-salt culture medium.

2) Preparation of the inoculum: The inoculum consists of a 24-hour-old culture of the test microorganism on a suitable agar nutrient medium diluted so as to obtain a suspension containing $10^8$ microorganisms/ml. A counting of 5 inocula is carried out.

3) Preparation of the sample: 20 g of the test product are placed in 5 glass flasks known as pill bottles.

4) Inoculation: 0.2 ml of inoculum of each strain is placed in a different pill bottle and homogenized. A contamination with $10^6$ microorganisms/g is thus obtained. The pill bottles are then incubated at 22° C. for 7 days.

5) Sampling and counting:

After incubating for 7 days, 1 g of product is taken from each of the pill bottles. Tenfold dilutions are carried out in a diluent containing preservative inhibitors which will stop the action of the preserving agents. These dilutions are plated out on the surface of agar Petri dishes and are then incubated at 35° C. Counting is carried at 7 days.

The number of microorganisms must be less than 100 for the preserving system to be satisfactory.

2nd step: on the impregnated wipes

Inoculation of 250 gl of the following five strains:

*Pseudomona aeruginosa* (bacterium)

*Staphylococcus aureus* (bacterium)

*Escherichia coli* (bacterium)

*Aspergillus niger* (mould)

*Candida albicans* (yeast)

The composition whose count at 7 days is less than or equal to that of the control for all the microorganisms tested are considered as satisfactory and are noted as "compliant".

The other formulations are noted as "non-compliant".

The following combinations were tested:

| (1) Combination 1 according to the invention | |
|---|---|
| methyl p-hydroxybenzoate (methylparaben) | 0.2% |
| Quaternium-15 | 0.025% |
| disodium salt of ethylenediamine tetraacetic acid dihydrate | 0.1% |

| (2) Combination 2 (comparative example) | |
|---|---|
| methyl p-hydroxybenzoate (methylparaben) | 0.2% |
| propyl p-hydroxybenzoate (propylparaben) | 0.1% |
| chlorphenesin | 0.1% |
| sodium metabisulphite | 0.005% |

| (3) Combination 3 (comparative example) | |
|---|---|
| methyl p-hydroxybenzoate (methylparaben) | 0.2% |
| propyl p-hydroxybenzoate (propylparaben) | 0.1% |
| imidazolidinylurea | 0.25% |
| tetrasodium salt of ethylenediamine-tetraacetic acid containing 13% water | 0.05% |

| (4) Combination 4 (comparative example) | |
|---|---|
| polyhexamethylene-biguanide hydrochloride at 20% in water | 0.75% |

| (5) Combination 5 (comparative example) | |
|---|---|
| methyl p-hydroxybenzoate (methylparaben) | 0.2% |
| propyl p-hydroxybenzoate (propylparaben) | 0.1% |
| imidazolidinylurea | 0.3% |

| (6) Combination 6 (comparative example) | |
|---|---|
| 3-iodo-2-propynyl butyl carbamate in polyethylene glycol mono-di-cocoate and polyethylene glycol (4 EO) (10/40/40/10) | 0.15 |

In our bacteriological study, we used the preserving system below as reference:

| | |
|---|---|
| phenoxyethanol | 0.5% |
| methyl p-hydroxybenzoate (methylparaben) | 0.2% |
| disodium salt of ethylenediaminetetraacetic acid dihydrate | 0.05% |
| tetrasodium salt of ethylenediaminetetra-acetic acid containing 13% water | 0.05% |

The results obtained are collated in Table 1 below:

| | Reference | Combination 1 | Combination 2 | Combination 3 | Combination 4 | Combination 5 | Combination 6 |
|---|---|---|---|---|---|---|---|
| Methyl p-hydroxybenzoate | 0.2% | 0.2% | 0.2% | 0.2% | | 0.2% | |
| Propyl p-hydroxybenzoate | | | 0.1% | 0.1% | | 0.1% | |
| Phenoxyethanol | 0.5% | | | | | | |
| Quaternium-15 | | 0.025% | | | | | |
| Imidazolidinylurea | | | | 0.25% | | 0.3% | |
| Chlorphenesin | | | 0.01% | | | | |
| Sodium metabisulphite | | | 0.005% | | | | |
| Tetrasodium salt of ethylenediamine-tetraacetic acid containing 13% water | 0.05% | 0.1% | | 0.05% | | | |
| Disodium salt of ethylenediaminetetra acetic acid dihydrate | 0.05% | | | | | | |
| Polyhexamethylene-biguanide hydrochloride at 20% in water | | | | | 0.75% | | |

-continued

|  | Reference | Combination 1 | Combination 2 | Combination 3 | Combination 4 | Combination 5 | Combination 6 |
|---|---|---|---|---|---|---|---|
| 3-Iodo-2-propynyl butyl carbamate in polyethylene glycol mono-di-cocoate and polyethylene glycol (4 EO) (10/40/40/10) |  |  |  |  |  |  | 0.15% |
| Number of microorganisms for the fluid after 7 days | <100 | <100 | <100 | <100 | <100 | <100 | <100 |
| Number of microorganisms on the wipes after 7 days | Compliant | Compliant | Non-Compliant | Non-Compliant | Non-Compliant on *E. coli* | Non-Compliant on *P. aeruginosa* | Non-Compliant on *P. aeruginosa, S. aurueus* and *E. coli* |

The results show that only the system in accordance with the invention gives results equivalent to the reference, while at the same time giving products that pose no problems in terms of harmlessness.

COMPOSITION EXAMPLES

The examples below of compositions according to the invention are given as illustrations and with no limiting nature. The amounts therein are given as percentages by weight, except where otherwise mentioned.

EXAMPLE 1

Makeup-removing Milk (O/W Emulsion)

| Phase A: | |
|---|---|
| Glyceryl stearate/PEG-100 stearate (Arlacel 165) | 0.6% |
| Cetyl alcohol | 0.15% |
| Fragrance | qs |
| Phase B: | |
| Methylparaben | 0.2% |
| Disodium salt of ethylenediaminetetraacetic acid dihydrate | 0.1% |
| Demineralized water | qs 100% |
| Phase C: | |
| Carbomer | 0.1% |
| Xanthan gum | 0.1% |
| Isopropyl palmitate | 5% |
| Phase D | |
| Triethanolamine | 0.1 |
| Phase E | |
| Quaternium-15 | 0.025% |
| Demineralized water | 30% |

Procedure: phases A and B are separately heated at 75/80° C. Phase A is added to phase B with stirring, and this stirring is then maintained for 5 minutes. Phases C and D are then added, followed by cooling with stirring. Phase E is added at 30° C. The mixture is cooled to room temperature (about 25° C.) and a milk is obtained.

The wipes impregnated with this makeup-removing milk allow makeup to be removed from the face and the eyes without irritation, while at the same time having very good antibacterial conservation.

EXAMPLE 2

Makeup-removing Milk (PIT Emulsion)

| Phase A: | |
|---|---|
| Cetearyl isononanoate | 1.8% |
| Cetearyl alcohol | 0.75% |
| Oxyethyleneated (20 EO) cetearyl alcohol (Ceteareth 20) | 0.75% |
| Oxyethyleneated (12 EO) cetearyl alcohol (Ceteareth 12) | 0.05% |
| Glycerol | 0.25% |
| Glyceryl stearate | 0.25% |
| Benzoic acid | 0.1% |
| Cetyl palmitate | 0.05% |
| Fragrance | 0.1% |
| Demineralized water | 6% |
| Phase B: | |
| (C8/10/12/14/16)alkyl polyglucoside (1.4) as an aqueous 53% solution sold under the name Plantacare 2000 by Cognis | 0.1% |
| Methylparaben | 0.2% |
| Disodium salt of ethylenediaminetetraacetic acid dihydrate | 0.1% |
| Quaternium-15 | 0.025% |
| Demineralized water | qs 100% |

Procedure: Phase A is prepared by the known means for emulsifying according to the phase inversion temperature process (PIT technique). After cooling to room temperature, phase B is introduced with gentle non-shear stirring. According to one preferred preparation method, the mixture of cetearyl isononanoate, ceteareth-20, cetearyl alcohol, glyceryl stearate, glycerol, ceteareth-12 and cetyl palmitate, sold under the name Emulgade CM by the company Cognis, is used to prepare phase A. After introducing the fragrance into this mixture at room temperature, phase B is introduced just before impregnation of the supports.

EXAMPLE 3

Makeup-removing Lotion (Aqueous Lotion)

| | |
|---|---|
| Disodium cocoamphodiacetate (Miranol C2M CONC NP from Rhodia Chimie) | 1.2% |
| Hexylene glycol | 1% |
| Methylparaben | 0.1% |
| Dosodium EDTA | 0.1% |
| Quaternium-15 | 0.02% |
| Triethanolamine | 0.08% |
| Demineralized water | qs 100% |

Procedure: the demineralized water is heated to 80° C., followed by successive addition, with stirring, of the disodium cocoamphodiacetate, the hexylene glycol, the methylparaben and then the disodium EDTA. This mixture is cooled to 40° C. with stirring. At this temperature, the Quaternium-15 is added, followed by the triethanolamine. The mixture is cooled to 25° C. and the lotion is obtained.

A 70/30 viscose/polyester nonwoven, with a weight per unit area of 65 g/m², is impregnated with 325% by weight of composition relative to the weight of nonwoven, with the compositions of Examples 1 to 3, and is then cut into the form of rectangular wipes 150 cm×200 cm in size.

A polyurethane foam can also be impregnated, for example to 100% by weight of composition relative to the weight of foam, with the compositions of Examples 1 to 3. It will advantageously be in the form of a round compress 70 mm in diameter and 1.5 mm thick.

French patent application 0108284 filed Jun. 22, 2001, is incorporated herein by reference, as are all references, texts, standards, documents, applications and patents referred to above.

What is claimed is:

1. A wipe comprising (A) a nonwoven water-insoluble substrate and (B) a physiologically acceptable composition in contact with the substrate comprising water, from 0.01% to 0.05% by weight of N-(3-chloroallyl)hexaminium chloride relative to the total weight of the composition, from 0.005% to 0.3% by weight of $C_1$–$C_4$ alkyl para-hydroxybenzoate relative to the total weight of the composition, and from 0.01% to 0.2% by weight of ethylenediaminetetraacetic acid salt relative to the total weight of the composition.

2. The wipe according to claim 1, wherein the composition comprises from 0.01% to 0.03% by weight of N-(3-chloroallyl)hexaminium chloride relative to the total weight of the composition.

3. The wipe according to claim 1, wherein the $C_1$–$C_4$ alkyl para-hydroxybenzoate is selected from the group consisting of methyl para hydroxybenzoate, ethyl para-hydroxybenzoate, propyl para-hydroxybenzoate, and mixtures thereof.

4. The wipe according to claim 1, wherein the $C_1$–$C_4$ alkyl para-hydroxybenzoate is methyl para-hydroxybenzoate.

5. The wipe according to claim 1, wherein the ethylenediaminetetraacetic acid salt is selected from the group consisting of the disodium salt of ethylenediaminetetraacetic acid, the tetrasodium salt of ethylenediaminetetraacetic acid, and mixtures thereof.

6. The wipe according to claim 1, wherein the composition has a viscosity of less than 100 mPa.s.

7. The wipe according to claim 1, wherein the composition is in the form of an aqueous or aqueous-alcoholic solution, an emulsion, a microemulsion, an aqueous or aqueous-alcoholic gel, or a vesicular dispersion.

8. The wipe according to claim 1, wherein the composition is in the form of an O/W emulsion.

9. The wipe according to claim 1, wherein the composition is in the form of a PIT emulsion.

10. The wipe according to claim 1, wherein said composition further comprises an emulsifier selected from the group consisting of fatty acid esters of polyols; oxyalkylenated fatty acid esters of polyols; fatty alcohol ethers of polyols; oxyalkylenated fatty alcohol ethers of polyols; and mixtures thereof.

11. The wipe according to claim 1, wherein said composition further comprises at least one adjuvant selected from the group consisting of organic solvents, solubilizing agents, thickeners and gelling agents, softeners, antioxidants, opacifiers, stabilizers, foaming agents, fillers, chelating agents, fragrances, screening agents, essential oils, dyestuffs, pigments, active agents and lipid vesicles.

12. The wipe according to claim 1, wherein said composition further comprises an active agent selected from the group consisting of antiseborrhoeic active agents, antimicrobial active agents, and mixtures thereof.

13. The wipe according claim 1, wherein said composition further comprises an antiseborrhoeic active agent selected from the group consisting of sulphur, sulphur compounds, benzoyl peroxide, zinc compounds, aluminium chloride, selenium disulphide, panthenol, niacinamide, and mixtures thereof.

14. The wipe according to claim 1, wherein said composition further comprises an antimicrobial active agent selected from the group consisting of 2,4,4'-trichloro-2'-hydroxydiphenyl ether, 3,4,4'-trichlorobanilide, phenoxyethanol, phenoxypropanol, phenoxyisopropanol, chlorhexidine and its salts, octopirox, zinc pyrithione, salicylic acid, 5-n-octanoylsalicylic acid, benzoyl peroxide, 3-hydroxybenzoic acid, glycolic acid, lactic acid, 4-hydroxybenzoic acid, acetylsalicylic acid, 2-hydroxybutanoic acid, 2-hydroxypentanoic acid, 2-hydroxyhexanoic acid, phytic acid, N-acetyl-L-cysteine acid, lipoic acid, azelaic acid, arachidonic acid, octoxyglycerol, octanoylglycine, caprylyl glycol and 10-hydroxy-2-decanoic acid, and mixtures thereof.

15. The wipe according to claim 1, wherein the composition further comprises at least one foaming surfactant.

16. The wipe according to claim 15, wherein the foaming surfactant is selected from the group consisting of oxyethylenated oxypropylenated block polymers, alkylpolyglucosides, alkyl sulphates, alkyl ether sulphates and salts thereof, alkylamido alkylamine derivatives, and mixtures thereof.

17. The wipe according to claim 1, wherein the composition is free of 2-pyrrolidone-5 carboxylic acid.

18. The wipe according to claim 1, wherein the composition has a pH from 6 to 7.5.

19. The wipe according to claim 1, wherein the composition is in the form of a lotion or a milk.

20. The wipe according to claim 1, comprising from 200% to 1000% by weight of said composition relative to the weight of said substrate.

21. The wipe according to claim 1, wherein said wipe is a skincare wipe and/or a skin treatment wipe.

22. The wipe according to claim 1, wherein said wipe is a wipe for cleansing and/or removing makeup from the skin and/or the eyes.

23. The wipe according to claim 9, wherein said composition is in the form of an ultrafine O/W emulsion.

24. A method for cleansing greasy skin or acne-prone skin, comprising wiping said skin with the wipe of claim 1.

25. A method for combating microorganisms in a cosmetic composition containing an aqueous phase and intended to impregnate a nonwoven water-insoluble substrate, comprising adding to said composition 0.01 to 0.05% by weight of N-(3-chloroallyl)hexaminium chloride relative to the total weight of the composition.

26. A method for cleansing and/or removing makeup from the skin and/or the eyes, comprising passing a wipe according to claim 1 over the skin and/or the eyes.

27. A dry wipe comprising a nonwoven water-insoluble substrate and, thereon, N-(3-chloroallyl)hexaminium chloride.

28. The dry wipe of claim 27, wherein N-(3-chloroallyl) hexaminium chloride is present in an amount from 0.01% to 0.05% by weight relative to the total weight of the wipe.

29. A method for cleansing greasy skin or acne-prone skin, comprising wiping said skin with a wipe comprising (A) a nonwoven water-insoluble substrate and (B) a physiologically acceptable composition in contact with the substrate comprising water, and from 0.01% to 0.05% by weight of N-(3-chloroallyl)hexaminium chloride relative to the total weight of the composition.

30. A method for cleansing and/or removing makeup from the skin and/or the eyes, comprising passing a wipe over the skin and/or the eyes, wherein the wipe comprises (A) a nonwoven water-insoluble substrate and (B) a physiologically acceptable composition in contact with the substrate comprising water, and from 0.01% to 0.05% by weight of N-(3-chloroallyl)hexaminium chloride relative to the total weight of the composition.

* * * * *

UNITED STATES PATENT AND TRADEMARK OFFICE
CERTIFICATE OF CORRECTION

PATENT NO.     : 6,784,145 B2
DATED          : August 31, 2004
INVENTOR(S)    : Patricia Delambre et al.

It is certified that error appears in the above-identified patent and that said Letters Patent is hereby corrected as shown below:

Title page,
Item [54], Title, delete "COMPRISING N-(3-CHLOROALLYL) HEXAMINIUM CHLORIDE"

Signed and Sealed this

Twenty-second Day of March, 2005

JON W. DUDAS
*Director of the United States Patent and Trademark Office*